United States Patent [19]

Van Nostrand et al.

[11] Patent Number: 5,427,931
[45] Date of Patent: Jun. 27, 1995

[54] MONOCLONAL ANTIBODY PRODUCED AGAINST NATIVE βAMYLOID PRECURSOR PROTEIN

[75] Inventors: William E. Van Nostrand, Irvine; Dennis D. Cunningham, Laguna Beach; Steven L. Wagner, Balboa Island, all of Calif.

[73] Assignee: Then Regents of the University of California, Oakland, Calif.

[21] Appl. No.: 56,423

[22] Filed: Apr. 27, 1993

Related U.S. Application Data

[60] Division of Ser. No. 924,417, Jul. 30, 1992, Pat. No. 5,213,962, which is a continuation of Ser. No. 513,786, Apr. 24, 1990.

[51] Int. Cl.$^6$ .............. C12P 21/08; A61K 39/395
[52] U.S. Cl. .............. 435/70.2; 435/70.21; 435/240.26; 435/240.27; 436/547; 436/548; 530/386; 530/388.15; 530/389.1; 530/388.1
[58] Field of Search .............. 435/70.2, 172.2, 240.26, 435/240.27, 70.21; 436/547, 548; 530/386, 387

[56] References Cited

U.S. PATENT DOCUMENTS 4,837,164  6/1989  Glick.

FOREIGN PATENT DOCUMENTS 304013  8/1988  European Pat. Off..
9014840  12/1990  WIPO.
9014841  12/1990  WIPO.

OTHER PUBLICATIONS

Weidemann et al.: Identification Biogenesis, and Localization of Precursors of Alzheimer's Disease A4 Amyloid Protein *Cell* vol. 57 pp. 115-126, Apr. 7, 1989.
Van Nostrand, W. E., and Cunningham, D. D., *J. Biol. Chem.*, 262:8508-8514 (1987).
Baker, J. B., et al., *Cell*, 21:37-45 (1980).
Wagner, S. L., et al. *Biochemistry*, 27:2173-2176 (1988).
Bradford, M. M., *Anal. Biochem.*, 72:248-254 (1976).
Laemmli, *Nature*, 227:680-685 (1970).
Potempa, et al., *Science*, 241:699-700 (1988).
Homsen et al., *Anal. Biochem.*, 46:489-501 (1972).
Rucinski et al., *Blood*, 53:47-62 (1979).
Wroblewski and Ladue, *Proc. Soc. Exper. Biol. Med.*, 90:210-213 (1955).
Schmaier, et al., *J. Clin. Invest.*, 75:242-250 (1985).
Laurell, *Anal. Biochem.*, 15:45-52 (1966).
de Duve et al., *Biochem. J.*, 60:604-617 (1955).
Weissbach et al., *J. Biol. Chem.*, 230:865-871 (1955).
Weidemann et al., *Cell*, 57:115-126 (1989).
Joachim et al., *Nature*, 341:226-230 (1989).
Palmert et al., *Science*, 241:1080-1084 ((1988).
Kang et al., *Nature*, 325:733-736 (1987).
Goldgaber et al., *Science*, 235:877-884 (1987).
Ponte et al., *Nature*, 331:525-532 (1988).
Dyrks et al., *The Embo Journal*, 7:949-957 (1988).
Shivers et al., *The Embo Journal*, 7:1365-1370 (1988).
Tate-Ostroff et al., *Proc. Natl. Acad. Sci. USA*, 86:745-749 (1989).
Hooper, C., *J. NIH Res.*, 1:88-93 (1989).

(List continued on next page.)

*Primary Examiner*—Christine M. Nucker
*Attorney, Agent, or Firm*—Knobbe Martens Olson & Bear

[57] ABSTRACT

Monoclonal antibody and the hybridoma producing the antibody are disclosed. The antibody is produced against an epitope on native secreted forms of βAPP. A characteristic of the antibody is that the antibody specifically binds to at least one protein in culture medium in which neuroblastoma cells have been grown. This protein co-migrates in non-reducing polyacrylamide gel electrophoresis with PN-2 isolated from human fibroblast cultures. Other characteristics of the antibody are that the antibody specifically binds to PN-2 and to the secreted form of βAPP lacking the Kunitz-type inhibitor domain, the antibody selectively binds to neuritic plaques, and the antibody is sufficiently sensitive to detect secreted forms of βAPP in CSF, down to a total concentration of the secreted forms of βAPP of 3.75 μg/ml or lower.

2 Claims, 9 Drawing Sheets

```
                10                  20                  30                  40
βAPP    M L P G L A L L L L A A W T A R A L E V P T D G N A G L L A E P Q I A M F C G R

PN-2                                    L E V P T D G N A G L L A E P Q I A M F C G R 50                  60                  70                  80
βAPP    L N M H M N V Q N G K W D S D P S G T K T C I D T K E G I L Q Y C Q E V Y P E L

PN-2    L N M F M N V Q N G K W D S D P S G T K T C I D T K E G I L Q Y
              ↑

90                 100                 110                 120
βAPP    Q I T N V V E A N Q P V T I Q N W C K R G R K Q C K T H P H F V I P Y R C L V G

PN-2                                                    T X P H F V I P Y R
```

OTHER PUBLICATIONS

Carrell, R. W., *Nature,* 331:478–479 (1988).
Coria, F., et al., *Laboratory Investigation,* 58:454–458 (1988).
Marotta, C. A., et al. *Proc. Natl. Acad. Sci. USA,* 86:337–341 (1989).
Jean Marx, Science, vol. 256, Research News, May 29, 1992.
Kitaguchi et al., Determination of Amyloid B Protein Precursors . . . , Bioch. Biophys. Res. Comm., 166:1453–1459 (1990).
Ghiso et al., Alzheimer's Disease Amyloid Precursor Protein is Present in Senile Plaques and Cerebrospinal Fluid, Bioch. Biophys. Res. Comm., 163:430–437 (1989).
Weidemann et al., Identification, Biogenesis, and Localization of Precursors of Alzheimer's Disease A4 Amyloid Protein, Cell, 57:115–126 (1989).
Van Nostrand, et al.; Dept. of Microbiology and Molecular Genetics; University of California: Irvine, Calif.; "Protease Nexin II In Human Platelets"; XIth International Congress on Thormhosis & Haemostatis, Brussels, Belgium; Jul. 6–10, 1987.
Nature, vol. 341, Oct. 12, 1989 "Protease nexin–II, a potent anti–chymotrypsin, shows identity to amyloid B–protein precursor".
Grubb, et al., "Abnormal Metabolism of $\gamma$–Trace Alkaline Microprotein" *Medical Intelligence,* 311:1547–1549 (1984).

FIG. 1

```
βAPP   M L P G L A L L L L A A W T A R A L E V P T D G N A G L L A E P Q I A M F C G R
                        10                  20                  30              40
PN-2                                         L E V P T D G N A G L L A E P Q I A M F C G R

βAPP   L N M H M N V Q N G K W D S D P S G T K T C I D T K E G I L Q Y C Q E V Y P E L
                        50                  60                  70              80
PN-2   L N M F M N V Q N G K W D S D P S G T K T C I D T K E G I L Q Y
            ↑

βAPP   Q I T N V V E A N Q P V T I Q N W C K R G R K Q C K T H P H F V I P Y R C L V G
                        90                 100                 110             120
PN-2                                                             T X P H F V I P Y R
```

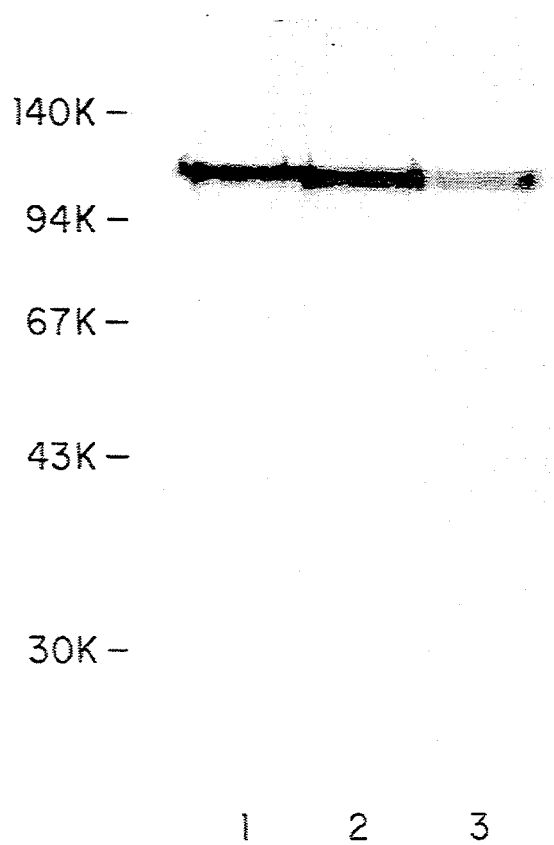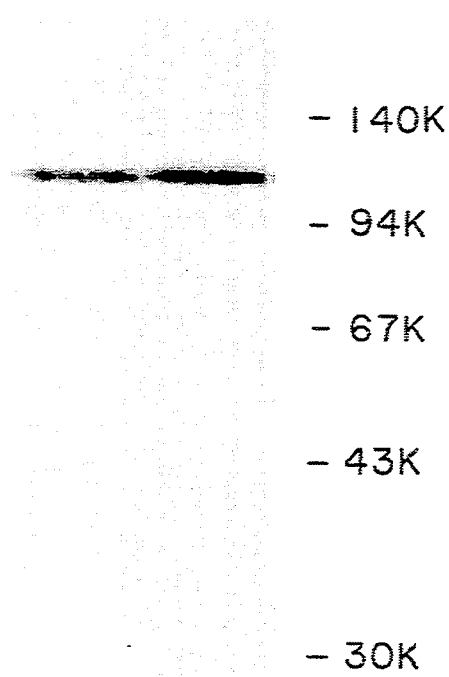

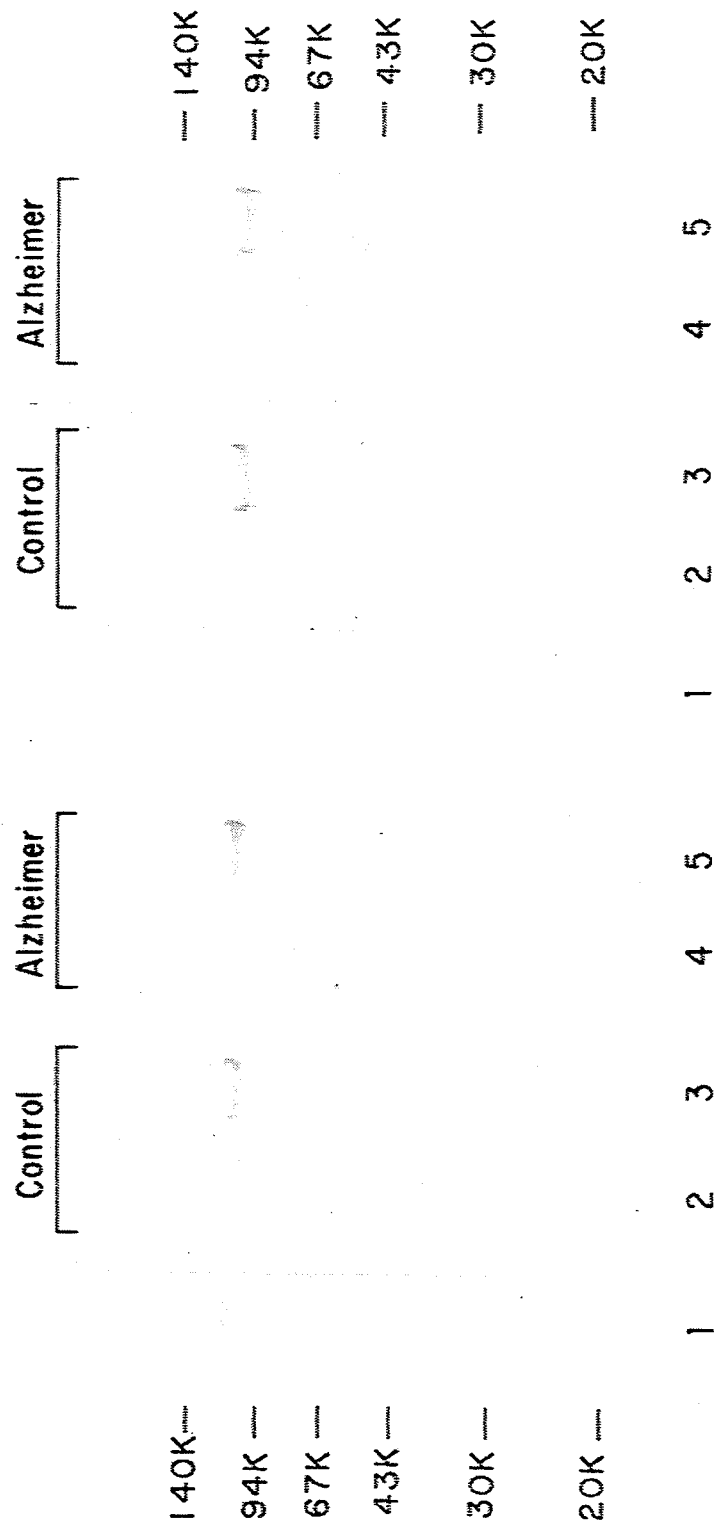

MONOCLONAL ANTIBODY PRODUCED AGAINST NATIVE βAMYLOID PRECURSOR PROTEIN

RELATED APPLICATIONS

The present application is a divisional of application Ser. No. 07/924,417, filed Jul. 30, 1992, which is a continuation of application Ser. No. 07/513,786, filed Apr. 24, 1990, and now abandoned.

BACKGROUND OF THE INVENTION

The present invention relates generally to the field of proteins associated with neural lesions. More specifically, the present invention relates to the purification, detection and methods of use of protease nexin-2 (hereinafter "PN-2").

This invention was made with Government support under Grant No. GM-31609 awarded by the National Institutes of Health. The Government has certain rights in this invention. American Cancer Society Grants CD 390 and BC 602/BE 22A provided further support for the development of this invention.

The protease nexins are protein proteinase inhibitors that are synthesized and secreted by a variety of cultured extravascular cells. PN-2 is a soluble, acidic protein fragment which forms stoichiometric, inhibitory complexes with several serine proteinases including, but not limited to, epidermal growth factor binding protein (EGF BP), the gamma subunit of 7S nerve growth factor (NGF-γ) and trypsin. In contrast to most serine proteinase inhibitors, PN-2 is very stable, retaining its inhibitory activity after treatments with SDS and pH 1.5.

PN-2 is believed to be derived from the μ-amyloid precursor protein (hereinafter "βAPP"). βAPP is known to be associated with neural lesions of Alzheimer's disease and Down's syndrome. βAPP comprises about 695 amino acid residues and has the characteristics of a cell receptor protein, comprising cytoplasmic, transmembrane and extracellular domains. Alternatively spliced forms of this precursor protein further comprise a 57 residue insert which is homologous to that of a "Kunitz-type" protease inhibitor which inhibits trypsin.

We have previously purified PN-2 from serum-free culture medium that was conditioned by human fibroblasts. However, this material was slightly contaminated with other components. Thus, there is a need for an improved method for purifying PN-2.

Alzheimer's disease is characterized by the accumulation of amyloid protein both intracellularly and extracellularly in the tissues of the brain, notably in neuritic plaques. The major protein subunit of these amyloid plaques has been identified as a polypeptide of about 4.5 kD having the ability to aggregate. This protein subunit is variously referred to as the amyloid β-protein or as amyloid A4, and is herein referred to as "A4".

A4 is thought to have its origin, through proteolytic cleavage, in βAPP. Release of the A4 unit is thought to occur by proteolysis of the precursor which may result from membrane damage. Because A4 is believed to be critical to the formation of amyloid plaques, there is a need for methods of preventing the release of A4.

The cDNA for βAPP lacking the Kunitz domain has been cloned and the nucleotide sequence determined. From the nucleotide sequence, the amino acid sequence has been predicted. The A4 peptide lies at residues 597 to 648 of the deduced amino acid sequence.

Alzheimer's disease produces a debilitating dementia for which no treatment is known. Thus, there is a need for methods of treatment and prevention of this disease.

Down's syndrome is a genetic disease which usually causes mental retardation and other symptoms. An unusually after the age of 40. Thus, there is a need for a treatment for Down's.

Presently, definitive diagnosis of Alzheimer's disease is only available at autopsy. Such diagnosis involves examination of brain tissue for extracellular neuritic plaques and intracellular tangles of microtubule-associated proteins and other cytoskeletal elements. The plaques are believed to start to form years before any clinical sign of Alzheimer's appears.

Many researchers believe that there is a correlation between the density of neuritic plaques and the severity of dementia. Thus, there is a need for preventing further development of neuritic plaques. If applied prior to the development of Alzheimer's symptoms, such a treatment, may thereby prevent onset of the disease.

Even without a treatment for Alzheimer's, an early diagnosis of the disease would allow physicians to rule out other causes of dementia. Moreover, in order to study the genetics of Alzheimer's it would be very useful to obtain a diagnosis of the disease prior to autopsy. More importantly, once treatments are developed, an early diagnosis may prove critical in the treatment's ability to improve mental functioning. Thus, there is a need for a method for the early diagnosis of Alzheimer's.

SUMMARY OF THE INVENTION

Briefly, the present invention provides a method for detecting circulating levels of amyloid precursor protein and related fragments. The method comprises obtaining platelets from a patient and determining the presence or level of amyloid precursor protein in the platelets. In a preferred method, the platelets are lysed prior to determining the level of amyloid precursor protein, The platelets may also be activated with a platelet agonist, such as thrombin or collagen.

In accordance with one aspect of the present invention, there is provided monoclonal antibodies specific to protease nexin-2 or beta amyloid precursor protein (PN-2/βAPP) and a hybridoma cell line producing the antibody.

The present invention also provides a method of diagnosing a neurodegenerative condition which comprises obtaining platelets from a patient, determining the level of PN-2/βAPP or a fragment thereof in the platelets, and comparing the level determined with normal levels.

The present invention also provides a method for detecting abnormal levels of PN-2/βAPP and related fragments in a mammal, comprising obtaining a sample of cerebral spinal fluid from a mammal, measuring the level of PN-2/βAPP or related fragments in the sample, and comparing the measured level with normal levels.

Additionally, the present invention provides a method for inhibiting deposition of amyloid plaques in a mammal, comprising the administration to the mammal of an effective plaque-deposition inhibiting amount of protease nexin-2 or a fragment or analog thereof.

The present invention, further, provides a method for inhibiting factor XIa in a mammal, comprising the administration of an effective factor XIa inhibiting amount of protease nexin-2 or a fragment or analog thereof.

Pharmaceutical compositions for use in any of the methods of the present invention are also provided, comprising protease nexin-2 or any fragment or analog thereof and a pharmaceutically acceptable diluent, carrier or excipient.

Furthermore, the present invention provides a method of diagnosing Alzheimer's disease at autopsy, comprising immunostaining brain tissue with an antibody to protease nexin-2 and determining the presence of Alzheimer's disease by the presence of reagents stained by the antibody.

Further objects, features and other advantages of the present invention will become apparent from the ensuing detailed description, considered together with the appended figures.

DESCRIPTION OF THE FIGURES

FIG. 1 shows the alignment of PN-2 and βAPP amino acid sequences, showing identity of PN-2 amino acid sequences within segments of the first 120 amino acids of the deduced βAPP sequence.

FIGS. 2a and b show immunoblot analysis of PN-2 in cell culture media and brain tissue homogenates. a, Monoclonal antibody mAbP2-1 stained identical proteins in PN-2enriched culture medium from normal human fibroblasts (lane 1), human glioblastoma cells (lane 2) and human neuroblastoma cells (lane 3). b, This same monoclonal antibody stained apparently identical proteins in tissue homogenates from normal (lane 1) and Alzheimer's disease (lane 2) brain.

FIGS. 7a–d shows Western blots of PN-2/βAPP in plasma and platelet lysates.

FIGS. 8A 1-3 and 8B 1-4 show Platelet subcellular fractionation and localization of PN-2/βAPP.

DETAILED DESCRIPTION OF THE PREFERRED EMBODIMENT

IMMUNOPURIFICATION OF PN-2

Figure 3A:
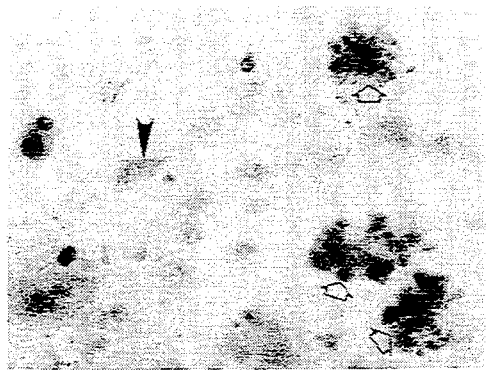
FIGS. 3a and b show immunostaining of Alzheimer's disease neuritic plaques with monoclonal antibody mAbP2-1. a, Photomicrograph showing strong immunoperoxidase reaction for PN-2 in scattered neuritic plaques (open arrows) within the CA1 region of the hippocampus of a 62-year-old female patient with Alzheimer's disease. Solid arrow points to a pyramidal neuron Vibratome section (40 μm) viewed by bright field microscopy. X200. b, Photomicrograph of a neuritic plaque on higher magnification showing strong immunoperoxidase reaction for PN-2 (open arrow) within the CA1 region of the hippocampus. Solid arrows point to pyramidal neurons. Vibratome section (40 μm) viewed by Nomarsky interference microscopy. X1,000.

We have discovered the PN-2 specific monoclonal antibody producing hybridoma cell line mAbP2-1. We have further discovered an improved method for purifying PN-2 employing the monoclonal antibody produced by this cell line in an immunoaffinity step. In this method, we retained the primary dextran sulfate-Sepharose affinity step from our initial purification scheme reported in Van Nostrand, W. E., and Cunningham, D. D. *J. Biol. Chem.*, 262: 8508–8514 (1987), the disclosure of which is hereby incorporated by reference. This step was retained because the step provides an effective means of concentrating the large volume of starting serum-free conditioned culture medium and enriches for PN-2.

The pooled PN-2-containing fractions from the primary dextran sulfate-Sepharose affinity step were then directly applied to a mAbP2-1 monoclonal antibody immunoaffinity column. After washing, apparently homogenous PN-2 was eluted with low pH buffer. The overall activity yield from numerous purifications was between 70–85%. Importantly, only PN-2 can be detected with mAbP2-1 in the starting conditioned culture medium or pooled dextran sulfate-Sepharose fractions; further demonstrating its specificity, as well as sensitivity. The specificity of monoclonal antibody mAbP2-1 facilitated the purification of PN-2 from complex starting solutions such as tissue homogenates. The following examples describe the immunopurification and testing of purified PN-2.

EXAMPLE 1—Preparation of Column for Immunopurification of PN-2

Normal human neonatal foreskin fibroblasts were isolated from explants and cultured as previously described by Baker, J. B., et al., *Cell*, 21:37–45 (1980). Four liters of serum-free medium from microcarrier cultures of human fibroblasts were collected and chromatographed over a dextran sulfate-Sepharose affinity column.

The PN-2 specific monoclonal hybridoma cell line mAbP2-1, ATCC No. HB 10424, was prepared following procedures we described in Wagner, S. L. et al. *Biochemistry* 27:2173–2176 (1988), the disclosure of which is hereby incorporated by reference. Monoclonal antibody mAbP2-1 was purified from ascites fluid using an Affi-Gel Protein A MAPS Kit (BioRad Laboratories) and coupled to cyanogen bromide activated-Sepharose 4B (Pharmacia Biochemicals) as described by the manufacturer. A 4 ml column of mAbP2-1Sepharose equilibrated with 20 mM potassium phosphate, 1M NaCl, pH 7.4 was prepared.

EXAMPLE 2—Immunopurification of PN-2

PN-2-containing fractions from the dextran sulfate column were directly applied to the mAbP2-1-Sepharose column at a flow rate of 10 ml/h. After the column was loaded, it was washed with five column volumes of 20 mM potassium phosphate, 1M NaCl, pH 7.4, followed by two column volumes of 20 mM potassium phosphate, 0.15M NaCl, pH 7.4. The adsorbed PN-2 was eluted from the immunoaffinity column with 0.2M glycine-HCl, 0.15M NaCl, pH 2.8. 750 μl fractions were collected in tubes containing 75 μl of 2M Tris-HCl, pH 8.3 to neutralize the elution buffer. During the purification, protein concentrations were determined by the method of Bradford, M. M., *Anal. Biochem.* 72:248–254 (1976), the disclosure of which is hereby incorporated by reference.

EXAMPLE 3—PN-2 Activity Assay

In order to quantify the immunopurification of Example 1, known quantities of $^{125}$I-EGF BP were incubated with aliquots of samples containing PN-2 for 15 minutes at 37° C. An equal volume of SDS-PAGE sample buffer was added and the mixtures were subjected to SDS-PAGE. After autoradiography, PN-2 activity was monitored by the formation of a 120-kDa complex with the $^{125}$I-EGF BP. To quantitate PN-2 activity, the autoradiograms were aligned with the dried gels and the $^{125}$I-labeled complexes were located, excised and measured in a gamma counter. Units were expressed as pMoles of $^{125}$I-EGF BP complexed.

SEQUENCE ANALYSIS OF PN-2

TABLE I

| | | | Immunopurification of PN-2 | | | |
|---|---|---|---|---|---|---|
| STEP | VOLUME (ml) | PROTEIN (mg) | UNITS | SPECIFIC ACTIVITY (units/mg) | YIELD (%) | PURIFICATION -fold |
| onditioned medium | 4,000 | ~4,600 | 1,139 | 0.25 | 100 | 1 |
| extran ulfate-epharose | 280 | 152 | 1,089 | 72 | 95 | 286 |
| AbP2-1 epharose | 8.5 | 0.175 | 861 | 4,920 | 76 | 19,680 |

We have performed amino terminal amino acid sequence analysis on two peptides obtained from digestion of PN-2. The analysis revealed that PN-2 has sequence identity with βAPP. The methods employed in this analysis are described in the following example.

EXAMPLE 4–Amino Acid Sequence Analysis of PN-2

Approximately 2 nmoles of purified PN-2 were digested with either CNBr or endoproteinase Lys-C (available from Boehringer Mannheim). The resulting peptides were subjected to SDS-polyacrylamide gel electrophoresis as described in Laemmli, *Nature*, 227:680–685 (1970). The peptides were electroeluted from the gels onto Immobilon polyvinylidene difluoride membranes (available from Millipore) in a Transblot unit (available from BioRad Laboratories). After transfer, the membranes were stained with Coomassie Brilliant Blue R-250, destained and soaked in several changes of distilled water. A 12 kilodalton ("KD") CNBr peptide and a 20 KD endoproteinase Lys-C peptide were excised from the membranes and directly subjected to amino terminal amino acid sequence analysis using an Applied Biosystems 473-A Gas Phase Sequencer with an on-line microbore PTH-amino acid separator and data analyzer (available from Applied Biosystems in models 120-A and 900-A). The sequence determined is shown in FIG. 1.

The protein sequence database of the National Biomedical Research Foundation was searched with the PN-2 amino acid sequence data obtained from Example 4, and identity was found within the deduced sequence for βAPP. Accordingly, the deduced sequence for βAPP is shown in alignment with PN-2 sequences in FIG. 1.

Figures 1, 8A:
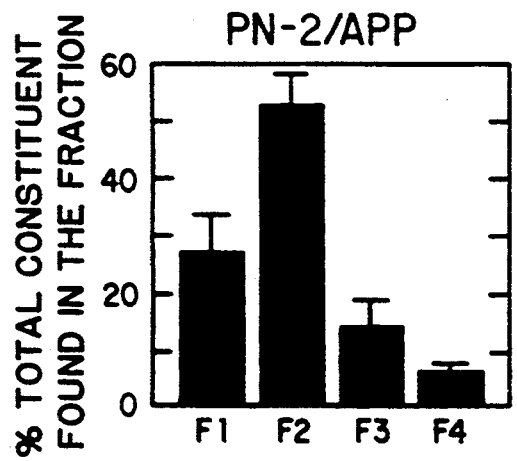

As seen in FIG. 1, the amino terminus of PN-2 starts at position 18 of βAPP. Underlined PN-2 residues at positions 46–72 were derived from the PN-2 CNBr peptide. Bold PN-2 residues at positions 46–50 represent overlap from the amino terminal sequence of native PN-2 and the amino terminal sequence of the PN-2 CNBr peptide. The arrow at position 44 represents an uncertain phenylalanine from the original amino terminal sequence of native PN-2 and is the only discrepancy in the alignments. Underlined PN-2 residues at positions 107–116 were derived from a PN-2 endoproteinase Lys-C peptide. No determination could be made for position 108 of PN-2.

IDENTITY OF PN-2 AND βAPP

FIG. 1 reveals that the only discrepancy between βAPP and PN-2 was at amino acid residue 27 of PN-2. The βAPP cDNA predicts a histidine residue at the position corresponding to position 27 of PN-2, which we reported as a questionable phenylalanine. Based on the observed sequence identity along with reports that certain forms of βAPP possesses a proteinase inhibitory domain and proteinase inhibitory activity, we believe that PN-2 and a secreted form of βAPP containing the Kunitz inhibitor domain are the same or very similar proteins.

Cultured human glioblastoma cells and neuroblastoma cells have been shown to express mRNA for βAPP and to secrete the protein. βAPP mRNA and protein have also been detected in human brain. To further confirm our belief that PN-2 and βAPP were the same or similar proteins, immunoblot analysis for PN-2 was performed using these cell lines, as in the following example.

EXAMPLE 5—Immunoblot Analysis of PN-2

A PN-2-specific monoclonal hybridoma cell line was prepared as in Example 1. Normal human neonatal foreskin fibroblasts, human glioblastoma HTB-14 and human neuroblastoma HTB-11 cells were cultured in Dulbecco's Modified Eagle Medium containing 10% fetal bovine serum and antibiotics. Serum-free medium from the cultured cells was concentrated and enriched for PN-2 by passing 100 ml of medium through a 1 ml DEAE-Sepharose column; the adsorbed protein was eluted with 2 ml of 1M NaCl. Human brain parietal cortex sections were placed in a buffer (20 ml/gm tissue) containing 200 mM NaCl, 20% glycerol, 1% Triton X-100 and 20 mM potassium phosphate, pH 7.4, homogenized for 5 minutes using a Polytron and centrifuged at 10,000 x g for 15 minutes at 4° C. to remove particulates. For immunoblots, samples were subjected to SDS-PAGE; completed gels were soaked in transfer buffer and the proteins were electroeluted onto Immobilon polyvinylidene difluoride membranes for 2.5 hours at 0.4A in a Transblot unit. The membranes were gently agitated in TBS (50 mM Tris-HCl, 150 mMNaCl, pH 7.5) containing 0.25% gelatin overnight at 25° C. to block unoccupied sites followed by incubation with mouse monoclonal mAbP2-1 hybridoma culture supernatant for 1 hour at 37° C. with gentle agitation. After several washes with TBS containing 0.05% Tween-20, bound mouse mAbP2-1 was detected with a biotinylated-sheep anti-mouse IgG (Amersham) and a streptavidin-horseradish peroxidase complex with several washes between each step. To develop the immunoblots, 48 mg of 4-chloronapthol were dissolved in 16 ml of ice-cold methanol and this was added to 80 ml of ice-cold TBS followed by the addition of 64 $\mu$l of $H_2O_2$. The developed immunoblots are shown in FIG. 2a.

Figures 2, 8A:
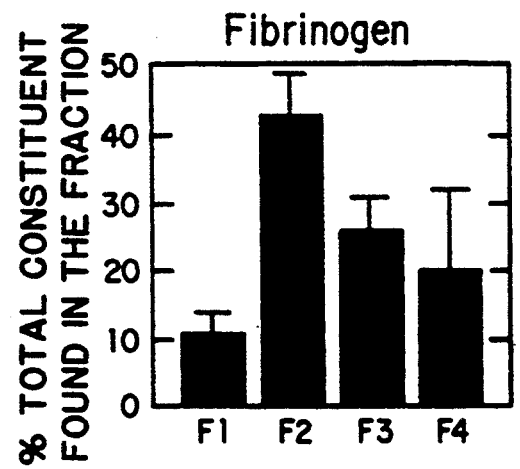

The immunoblots of FIG. 2a show that the PN-2specific monoclonal antibody mAbP2-1 recognized a protein in the culture medium of glioblastoma cells (lane 2) and neuroblastoma cells (lane 3), cells known to secrete $\beta$APP. Moreover, it can be seen that the protein recognized in both of these cell cultures co-migrated in SDS-PAGE with the PN-2 present in human fibroblast culture medium (lane 1). Thus, Example 5 provides further support for our belief that the secreted form of $\beta$APP containing the Kunitz inhibitor domain and PN-2 are the same or very similar proteins. Accordingly, the term "PN-2/$\beta$APP" will be used herein to refer to these proteins jointly.

USE OF mAbP2-1 IN THE DIAGNOSIS OF ALZHEIMER'S

We also used mAbP2-1 in immunoblots of tissue homogenates of the parietal cortex of healthy brain and of Alzheimer's disease brain. FIG. 2b shows these results; lane 1 is a blot of SDS-PAGE of parietal cortex homogenate of healthy brain and lane 2 of Alzheimer's brain. As can be seen in FIG. 2b, MAbP2-1 recognized a protein in tissue homogenates prepared from the parietal cortex of both healthy brain or Alzheimer's disease brain. Thus, the mere finding PN-2 immunoreactivity in brain tissue homogenates does not serve as an indication of Alzheimer's. However, immunostaining with mAbP2-1 will selectively stain neuritic plaques in tissue sections of Alzheimer's disease brain.

Thus, we have discovered that mAbP2-1 can be effectively used to diagnose Alzheimer's at autopsy. The following example shows a typical method for immunostaining brain tissue to reveal the presence of PN-2 immunoreactivity in Alzheimer's disease brain.

EXAMPLE 6—Immunostaining of Alzheimer's Disease Brain

Figures 3, 8A:
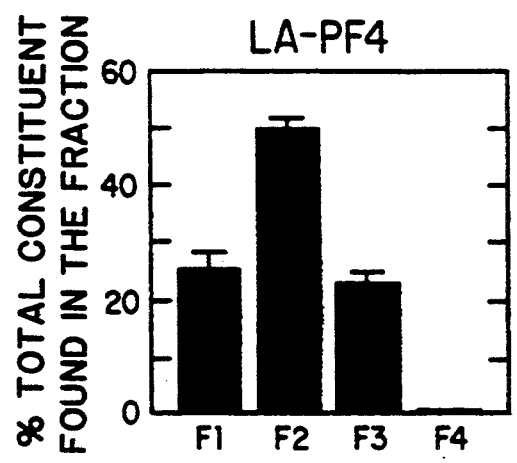

Tissues were fixed overnight in 2% paraformaldehyde and 0.01% glutaraldehyde. After washing in PBS, vibratome sections were prepared and subsequently processed using a avidin-biotin complex immunoperoxidase detection system for PN-2 which uses the PN-2-specific antibody mAbP2-1. Results are seen in FIG. 3.

Figure 3B:
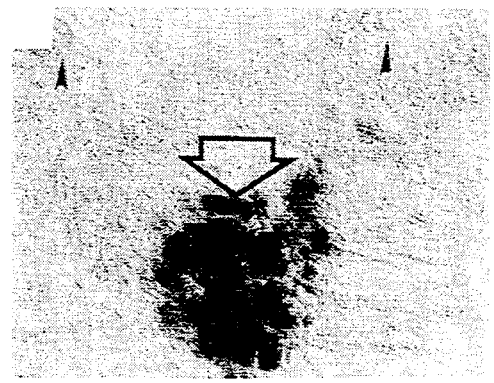

FIG. 3a shows that mAbP2-1 exhibited intense staining of neuritic plaques with the CA1 region of the hippocampus of a patient with Alzheimer's disease. Staining was not observed in age-matched controls (data not shown). Higher magnification of a neuritic plaque, seen in FIG. 3b, showed that the staining was more pronounced at the periphery.

Thus, Example 6 illustrates one method of diagnosing Alzheimer's at autopsy by the specific immunostaining of neuritic plaques with mAbP2-1.

PHYSIOLOGICAL FUNCTION FOR PN-2/$\beta$APP

Several considerations suggest that one physiological function for PN-2/$\beta$APP is the regulation of a chymotrypsin-like proteinase. One such consideration is derived from the finding that neuritic plaques in Alzheimer's disease contain A4 which is cleaved from $\beta$APP by proteolytic cleavage. Studies have shown that $\beta$APP can be translated from at least three alternatively spliced mRNAs, only two of which contain an insert encoding for a Kunitz-type protease inhibitor domain. Alzheimer's patients have been found to have an excess of mRNA coding for $\beta$APP lacking the Kunitz-type proteinase inhibitor domain. Thus, we believe that this proteinase inhibitor domain is critical in preventing the build-up of A4 in neuritic plaques.

Another consideration is that it has been reported that a methionine residue flanks the amino terminal side of the peptide bond that is cleaved upon release of A4 from $\beta$APP. This site is susceptible to cleavage by a chymotrypsin-like proteinase to release the A4 protein. Accordingly, we believe that one physiological function of PN-2/$\beta$APP is the inhibition of this chymotrypsin-like proteinase.

We tested the ability of purified PN-2 to inhibit a variety of serine proteinases employing spectrophotometric assays with chromogenic substrates. We found that PN-2 was a potent inhibitor of chymotrypsin. Although the formation of complexes between chymotrypsin and PN-2 was not observed by SDS-PAGE, stable chymotrypsin-PN-2 binding was identified with a $^{125}$I-chymotrypsin blotting assay. The following is an example of such an assay.

EXAMPLE 7–$^{125}$I-Chymotrypsin Blotting Assay

Figure 4:
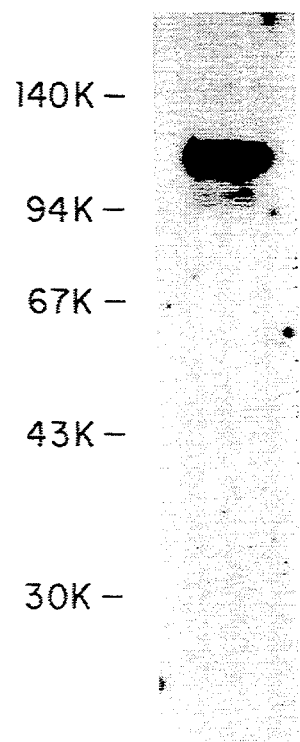
FIG. 4 shows the binding of $^{125}$I-chymotrypsin to PN-2 after the latter was subjected to SDS-PAGE and transferred to a nitrocellulose membrane.

Two $\mu$g of purified PN-2 were subjected to SDS-PAGE according to Laemmli, supra. The complete gel was soaked for 10 minutes in a transfer buffer consisting of 10 mM sodium bicarbonate, 3 mM sodium carbonate, 20% methanol, pH 9.9 and the PN-2 was electroeluted onto a nitrocellulose membrane for 2 hours at 400 mA in Transblot unit (available from BioRad Laboratories). After transfer, the nitrocellulose membrane was gently agitated overnight in a solution of TBS containing 0.25% gelatin to block unoccupied sites on the membrane and then incubated with a solution of TBS containing 20 ng/ml of $^{125}$I-chymotrypsin (specific activity $= 5.5 \times 10^5$ cpm/pmole) for 20 minutes at 25° C. followed by two 10 minutes washes with TBS containing 0.05% Tween-20 and a final wash in TBS. Membranes were dried and exposed to X-ray film for 12 hours at $-70°$ C. The resulting autoradiogram is shown in FIG. 4. The autoradiogram demonstrates that $^{125}$I-chymotrypsin bound to purified PN-2 that had been transferred to a nitrocellulose membrane after SDS-PAGE. A similar assay showed that $^{125}$I-chymotrypsin bound to PN-2 after SDS-PAGE of brain tissue homogenates and cell culture media from neuroblastoma and glioblastoma cells (data not shown).

To further examine the inhibition of chymotrypsin by PN-2 the inhibition equilibrium constant ($K_i$) was measured for the reaction. These studies revealed that PN-2 was a potent and reversible inhibitor of chymotrypsin with a $K_i = 6 \times 10^{-10}$M. Reversible inhibition is characteristic of the Kunitz-type serine proteinase inhibitors which are homologous to a domain in βAPP. Incubation of PN-2 with chymotrypsin resulted in proteolytically processed forms of PN-2 which still retained their ability to bind and inhibit chymotrypsin (data not shown). These results are similar to results reported for another Kunitz-type inhibitor, plasma inter-α-trypsin inhibitor. Thus, we concluded that, like βAPP, PN-2 has Kunitz-type inhibitor activity. To further test this conclusion, we performed further proteinase inhibition studies of the purified PN-2 from Example 1 on a variety of proteinases. The following example shows one such study in which PN-2 was found to be an effective inhibitor of both chymotrypsin-like and trypsin-like proteases.

PAGE without prior boiling, the kinetic studies indicate that these complexes are indeed reversible.

PN-2/βAPP was a potent inhibitor of the blood coagulation protease factor XIa. The finding that heparin enhanced the inhibition of factor XIa by PN-2/βAPP suggests that the other domains (i.e., heparin binding domains) may be important in the inhibition of certain target proteases. In addition, PN-2/βAPP effectively inhibited trypsin, chymotrypsin and two closely related serine proteases obtained from mouse submandibular gland, EGF BP and NGF-γ. Chymase and plasmin were inhibited to a lesser extent. PN-2/βAPP did not significantly inhibit plasminogen activators, tissue kallikrein, pancreatic elastase or several other proteases from the coagulation pathway.

TABLE II

| Inhibition constants for proteases and PN-2/APP | | |
|---|---|---|
| Protease (final molarity) | Substrate (final molarity) | $K_i$ (M) |
| Human factor XIa (5 nM) + heparin (10 U/ml) | Pyro-Glu-Pro-Arg-p-nitroanilide-hydrochloride (0.5 mM) | $5.5 \pm 0.3 \times 10^{-11}$ |
| Human factor XIa (5 nM) | Pyro-Glu-Pro-Arg-p-nitroanilide hydrochloride (0.5 mM) | $2.9 \pm 0.4 \times 10^{-10}$ |
| Bovine trypsin (5 nM) | Carbobenzoxy-Val-Gly-Arg-4-nitroanilide (0.5 mM) | $4.2 \pm 0.6 \times 10^{-10}$ |
| Bovine chymotrypsin (2.5 nM) | N-Succinyl-Ala-Ala-Pro-Phe-p-nitroanilide (0.25 mM) | $1.6 \pm 0.4 \times 10^{-9}$ |
| Mouse EGF-BP (10 nM) | H-D-Pro-Phe-Arg-p-nitroanilide dihydrochloride (0.5 mM) | $5.8 \pm 0.3 \times 10^{-9}$ |
| Mouse NGF-γ (10 nM) | H-D-Pro-Phe-Arg-p-nitroanilide dihydrochloride (0.5 mM) | $9.1 \pm 1.2 \times 10^{-9}$ |
| Human skin chymase (20 nM) | N-Succinyl-Ala-Ala-Pro-Phe-p-nitroanilide (0.5 mM) | $2.0 \pm 1.0 \times 10^{-8}$ |
| Human plasmin (10 nM) | Tosyl-Gly-Pro-Lys-4-nitroanilide (0.5 mM) | $2.9 \pm 0.6 \times 10^{-8}$ |
| Human thrombin (10 nM) | Tosyl-Gly-Pro-Arg-4-nitroanilide (0.5 mM) | not inhibited |
| Human factor XIIa (20 nM) | D-Hexahydro-Gly-Ala-Arg-4-nitroanilide diacetate (1 mM) | not inhibited |
| Human factor Xa (10 mM) | N-Methoxycarbonyl-D-norLeu-Gly-Arg-4-nitroanilide (1 mM) | not inhibited |
| Human plasm kallikrein (20 nM) | H-D-Pro-Phe-Arg-p-nitroanilide dihydrochloride (1 mM) | not inhibited |
| Human tissue kallikrein (20 nM) | D-Val-cyclohexylAla-Arg4-nitroanilide diacetate (0.5 mM) | not inhibited |
| Human urokinase (20 nM) | Benzoyl-β-Ala-Gly-Arg4-nitroanilide (0.5 mM) | not inhibited |
| Human tissue plasminogen activator (20 nM) | N-Methylsulfonyl-D-Phe-Gly-Arg-4-nitroanilide (1 mM) | not inhibited |
| Porcine pancreatic elastase (20 nM) | N-Methoxysuccinyl-Ala-Ala-Pro-Val-p-nitroanilide (1 mM) | not inhibited |

EXAMPLE 8—Proteinase-Blot Analysis of PN-2/βAPP

Aliquots of purified PN-2/βAPP were subjected to 10% SDS-PAGE and completed gels were soaked in transfer buffer (10 mM sodium bicarbonate, 3 mM sodium carbonate, 20% methanol, pH 9.9) for 10 minutes. The proteins were electroeluted from the gels onto nitrocellulose membranes for 2.5 hours at 0.4 A in a Transblot apparatus and then gently agitated in TBS containing 0.25% gelatin overnight at 25° C. to block unoccupied sites. The nitrocellulose membranes were then incubated with $^{125}$I-protease (20–50 ng/ml) for 30 minutes at 25° C. followed by two 10 minutes washes with TBS containing 0.05% Tween-20 and a final wash in TBS. Membranes were then air dried and exposed to X-ray film for 12–24 hours at −70° C. Results are shown in FIG. 5(a) and 5(b) and reported in Table II.

Figure 5B:
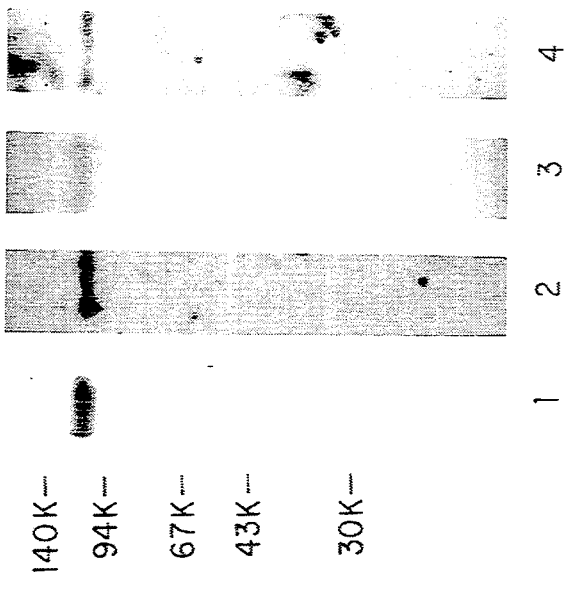
FIGS. 5a and b show $^{125}$I-protease-pN-2 complex formation. Panel A: 500 ng of purified PN-2 was incubated with 25 ng of $^{125}$I-labeled protease for 15 minutes at 37° C. The incubation mixtures were then analyzed for protease-PN-2 complexes by 10% SDS-PAGE without prior boiling of the samples and subsequent autoradiography. Lane 1, EGF BP; lane 2, EGF BP+PN-2; lane 3, NGF-7; lane 4, NGF-7+PN-2; lane 5, trypsin; lane 6, trypsin+PN-2. Panel B: 1 μg aliquots of purified PN-2 were subjected to SDS-PAGE; completed gels were transferred to nitrocellulose membranes, incubated with $^{125}$I-labeled protease, washed and autoradiography was performed. PN-2 labeled with: lane 1, $^{125}$I-chymotrypsin; lane 2, $^{125}$I-factor XIa; lane 3, $^{125}$I-plasmin; lane 4, $^{125}$I-chymase.
Figure 5A:
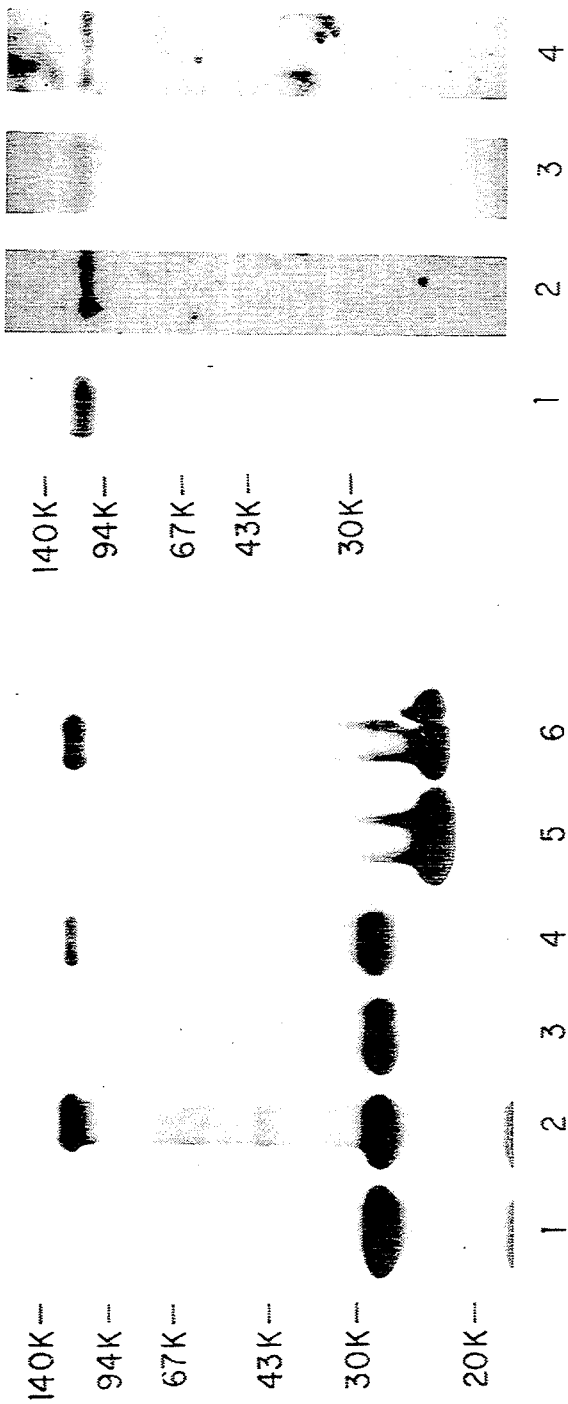

FIG. 5(a) shows that the low molecular weight "trypsin-like" proteases including EGF BP (lane 2), NGF-γ (lane 4) and trypsin (lane 6) formed SDS-stable complexes with PN-2/βAPP. In contrast, neither the higher molecular weight "trypsin-like" proteases factor XIa and plasmin nor "chymotrypsin-like" proteases chymotrypsin and chymase formed SDS-stable complexes with PN-2/βAPP (data not shown). We employed the protease blotting technique of Example 8 to demonstrate stable binding of this group of proteases to PN-2/βAPP.

FIG. 5(b) shows that $^{125}$I-labeled proteases bound to PN-2/βAPP that was immobilized on nitrocellulose. Thus Example 8 shows that a spectrum of different stabilities exist for complexes between PN-2/βAPP and the proteases it inhibits. Although complexes between certain proteases and PN-2/βAPP are stable in SDS-PAGE without prior boiling, the kinetic studies indicate that these complexes are indeed reversible.

The finding that PN-2/βAPP can inhibit serine proteases of two different class specificities is noteworthy. Factor XIa, trypsin, EGF BP, NGF-γ and plasmin are all "trypsin-like" in specificity in that they cleave peptide bonds on the carboxyl side of the basic amino acids lysine or arginine. In contrast, chymotrypsin and chymase preferentially cleave peptide bonds on the carboxyl side of large side chain amino acids. The deduced amino acid sequence of PN-2/βAPP aligned with other Kunitz-type serine protease inhibitors predicts Arg$^{301}$ to reside in the P$_1$ site of the reactive center. This is consistent with the inhibition of the "trypsin-like" proteases factor XIa, trypsin, EGF BP, NGF-γ and plasmin. In several instances strong inhibitors of trypsin with a P$_1$ Arg or Lys inhibit chymotrypsin at the same site. A similar mechanism may occur for inhibition of chymotrypsin and chymase by PN-βAPP. Alternatively, another site may be responsible for the inhibition of "chymotrypsin-like" proteases.

A recent study by Potempa, et al., Science, 241:699–700 (1988), the disclosure of which is hereby incorporated by reference, showed that α$_2$-antiplasmin can inhibit "trypsin-like" plasmin at the Arg$^{364}$-Met$^{365}$ bond or chymotrypsin at the adjacent Met$^{365}$-Ser$^{366}$ bond. It is possible that an adjacent site in PN-2/βAPP may be responsible for the "chymotrypsin-like" inhibition. We found that preformed EGF BP-PN-2/βAPP complexes did not inhibit chymotrypsin (data not shown) consistent with the possibility of identical or adjacent inhibitory sites. Alternatively, formation of EGF BP-PN-2/βAPP complexes may induce a conformational change in PN-2/βAPP that renders it inactive towards inhibiting of chymotrypsin.

Our discoveries that PN-2 is the same or very similar protein as βAPP and that PN-2/βAPP has a Kunitz-type inhibitor domain led us to a further discovery that PN-2/βAPP is useful in inhibiting the altered extracellular proteolysis implicated in Alzheimer's disease.

Thus, one aspect of the invention involves administration of PN-2/βAPP to a mammal to inhibit deposition of A4 in neuritic plaques. In this regard, we believe that administration of PN-2/βAPP in sufficient amounts to inhibit cleavage of PN-2/βAPP to release A4 is effective in inhibiting the deposition of neuritic plaques. Neuritic plaques are implicated in Alzheimer's, Down's, and possibly other diseases. Thus, we believe that administration of effective plaque-deposition inhibiting amounts of PN-2/βAPP are effective in the treatment and prevention of these diseases.

Accordingly, in certain preferred embodiments of the present invention, PN-2/βAPP is formulated into pharmaceutical preparations. These pharmaceutical preparations may further include other pharmaceutically active ingredients. In addition, any of the well-known pharmaceutically acceptable carriers or excipients may be combined with PN-2/βAPP in well-known manner. Administration may be intramuscular, intravenous, intraperitoneal, or by any other method suitable for delivering active pharmaceuticals to the body and to the brain.

Example 9 shows an exemplary therapeutic composition for administering PN-2/βAPP to a patient.

EXAMPLE 9—An Injectable Composition for Prevention of Alzheimer's 2 mg/ml PN-2/βAPP balance sterile H₂O Therapeutic dosages of PN-2/βAPP when used for intravenous injections in accordance with a method of the preferred embodiment is, preferably, the amount required to provide a level of PN-2/βAPP in the CSF in the patient of 1 µg/ml to 100 µg/ml. Levels of PN-2/βAPP can be assayed by the method of Example 20 described below. The levels of PN-2/βAPP in the CSF can also be measured quantitatively using the monoclonal antibody of the present invention in either a quantitative Western Blot or by an ELISA assay. Example 10 illustrates one immunological method of quantitating the level of PN-2/βAPP in CSF.

EXAMPLE 10—Western Blot for PN-2βAPP in Human CSF

Human CSF is obtained from a healthy human subject and subjected to SDS-PAGE. Standards having known amounts of PN-2/βAPP are also run on the gels. The resulting gels are transferred to nitrocellulose membranes and exposed to $^{125}$I labeled mAbP2-1. The membranes are exposed to film and the resulting autoradiograms are analyzed for the presence of PN-2/βAPP immunoreactivity using a scanner instrument. The CSF values are compared with those for the known standards to make a quantitative determination of the amount of PN- 2/βAPP in the CSF samples.

When using the pharmaceutical compositions of Example 10, the dose will depend on the level of PN-2/βAPP in the CSF of the patient. Thus, in the treatment of these patients, the CSF level of PN-2/βAPP immunoreactivity may be periodically monitored to keep the levels of PN-2/βAPP within the preferred therapeutic range. Example 11 illustrates a preferred method of the present invention of preventing Alzheimer's disease in a susceptible patient.

EXAMPLE 11—Prevention of Alzheimer's Disease with PN-2/βAPP

Five patients with very early stage Alzheimer's disease receive 1.0 cc of the composition of Example 9 intracranially once per day. A matched control group of five patients receive an equal amount of the composition of Example 9 without any active ingredient. The treatments are continued every day for a period of five years. Once per week for the first month, and once every three months thereafter, the level of PN-2/βAPP in each patient's CSF from the PN-2/βAPP group is monitored by the method of Example 10. The dosage is adjusted to keep the level of PN-2/βAPP within the range of 10 µg/ml to 100 µg/ml. At the end of five years, the PN-2/βAPP group is functioning well with little or no reduction in levels of ability to care for themselves or in memory. The control group exhibits significantly deteriorated memory and ability to care for themselves.

The foregoing examples show the utility of native PN-2/βAPP in effectively preventing further neurodegeneration associated with Alzheimer's. It is believed that administration of PN-2/βAPP in the manner of Example 11 will prevent any further neurodegeneration associated with Down's syndrome and other diseases as well. However, still greater effectiveness is believed obtainable from PN-2/βAPP which has been modified by deletion of some or all of the A4 region of native PN-2/βAPP. This is because native PN-2/βAPP not only provides the protease inhibiting domain of PN-2/βAPP but may also provide the A4 region itself.

Recent data suggests that PN-2/βAPP contains at least some of the A4 region. It is not known if normal PN-2/βAPP contains all of the A4 region. One theory is that normal PN-2/βAPP contains only a portion of the A4 region and that Alzheimer's patients may have the entire A4 domain. However, a competing theory is that both normal and Alzheimer's PN-2/βAPP contain the entire A4 domain, but that the A4 protein is cleaved from Alzheimer's PN-2/βAPP as the protein is extruded through cell membranes.

If the latter theory is correct, then it is believed that addition of PN-2/βAPP to a patient may have the unintended effect of providing more substrate for the release of A4. Thus, we believe that PN-2/βAPP lacking some or all of the A4 region may prove effective in inhibiting deposition of neuritic plaques in a mammal.

Example 12 shows an exemplary method of obtaining a modified PN-2/βAPP containing the entire Kunitz inhibitory domain and lacking all of A4.

EXAMPLE 12—Cloning and Expression of Modified PN-2/βAPP Lacking a Portion of the A4 Region A cDNA plasmid containing the gene for native PN-2/βAPP is obtained and the cDNA containing the native sequence is excised. A unique restriction site between the region coding for the Kunitz inhibitor domain and the A4 domain is located. The appropriate restriction enzyme is applied and the fragment containing the Kunitz inhibitor domain is isolated. An vector is chosen for expression of cloned sequences in yeast. Appropriate linker fragments are added to the Kunitz inhibitor domain containing fragment and the fragment is inserted into the vector. Expression in yeast produces the modified PN-2/βAPP.

Thus, Example 12 shows an exemplary method of cloning and expressing modified PN-2/βAPP. A similar method without the modification to the PN-2/βAPP gene can be employed to clone and express native PN-2/βAPP. As an alternative to the cloning and expression of modified PN-2/βAPP, it may be possible to cleave and isolate the Kunitz domain from PN-2/βAPP. This isolated protein fragment is expected to prove effective in preventing the deposition of amyloid plaques.

EXAMPLE 13—A Modified Composition Effective in Inhibiting Deposition of Neuritic Plaques 2 mg/ml modified PN-2/βAPP from Example 12
balance sterile $H_2O$

EXAMPLE 14—Prevention of Alzheimer's Disease

Five patients with very early stage Alzheimer's disease receive 1.0 cc of the composition of Example 9 intracranially once per day. A matched control group of five patients receive an equal amount of the composition of Example 13 without any active ingredient. The treatments are continued every day for a period of five years. At the end of five years, the PN-2/βAPP group is functioning well with no reduction in levels of ability to care for themselves or in memory. The control group exhibits significantly deteriorated memory and ability to care for themselves.

TABLE III

| | Secretion of PN-2/βAPP by Activated Platelets | | | |
|---|---|---|---|---|
| | Washed Platelets | | Inhibitor-Treated Platelets | |
| Markers | Collagen (%) | Thrombin (%) | Collagin (%) | Thrombin (%) |
| PN-2 | 46.3 ± 7.7 | 53.7 ± 7.6 | 0 | 0 |
| ADP/ATP | 45 ± 16 | 68 ± 11 | 1.3 ± 1.3 | 0 |
| LA-PF4 | 52 ± 11 | 69 ± 6.2 | 0 | 0.4 ± 0.4 |
| LDH | 1.3 ± 1.3 | 0 | 0 | 0 |

CIRCULATING SOURCE OF PN-2/βAPP

Deposition of A4 at sites of cerebrovascular malformations led us and others to conclude that abnormalities of blood vessel walls might lead to its deposition from the circulation. In addition, a recent report showed evidence for the deposition of A4 in non-neural tissues in Alzheimer's disease which also suggested the likelihood of a circulating source of A4. However, heretofore evidence for a plasma source of PN-2/βAPP or A4 has been lacking.

We have discovered the major circulating source of PN-2/βAPP by screening different fractions of whole blood employing functional and immunochemical assays. The functional assay was based on the ability of PN-2/βAPP to form SDS-stable complexes with EGF BP that can be detected after electrophoresis.

We looked for PN-2/βAPP in fractionated plasma and in platelet lysates prepared from fresh blood of a control and Alzheimer's disease patient. The functional assay we performed involved incubating the blood fractions with $^{125}I$ labeled EGF BP in order to allow complexes of PN-2/βAPP:EGF BP to form. SDS-PAGE was run and the complexes were detected as high molecular weight labeled bands. We could not detect PN-2/βAPP:EGF BP in the assays we performed on plasma. However, these complexes were detected in assays performed on platelet lysates taken from the same patients.

Before assaying the plasma, it was first fractionated over a DEAE-Sepharose anion exchange column to concentrate and enrich for PN-2/βAPP, as in Example 1. This step also removed the large amounts of albumin, immunoglobulins and other endogenous protease inhibitors. The following example shows a typical assay for PN-2/βAPP in platelet and plasma fractions.

EXAMPLE 15—PN-2/βAPP:EGF BP Complex Formation

Platelet poor plasma and platelets were prepared from freshly collected blood obtained from control and diagnosed Alzheimer's disease patients. Ten ml aliquots of plasma were diluted with 20 ml of 20 mM potassium phosphate, 0.2M NaCl, pH 7.4. As a control, purified PN-2/βAPP was added to some plasma aliquots at a final concentration of 0.5 nM. All plasma samples were then passed through 1 ml DEAE-Sepharose columns, the columns were then washed with 25 ml of the above buffer. Adsorbed proteins were eluted from the columns with 20mM potassium phosphate, 1M NaCl, pH 7.4. Platelets were resuspended to a final concentration of 0.5 to $1.0 \times 10^9$/ml and solubilized by incubation with 0.5% Triton X-100 for 30 minutes at room temperature. Aliquots of the DEAE-Sepharose eluates and platelet lysates were then incubated with 40 ng of $^{125}I$-EGF BP ($1.75 \times 10^6$ cpm/pmole) for 15 minutes at 37° C. An equal volume of SDS-sample buffer was added and the samples were subjected to nonreducing 10% SDS-PAGE as described by Laemmli, Supra. Completed gels were dried and autoradiograms were prepared.

Figure 6:
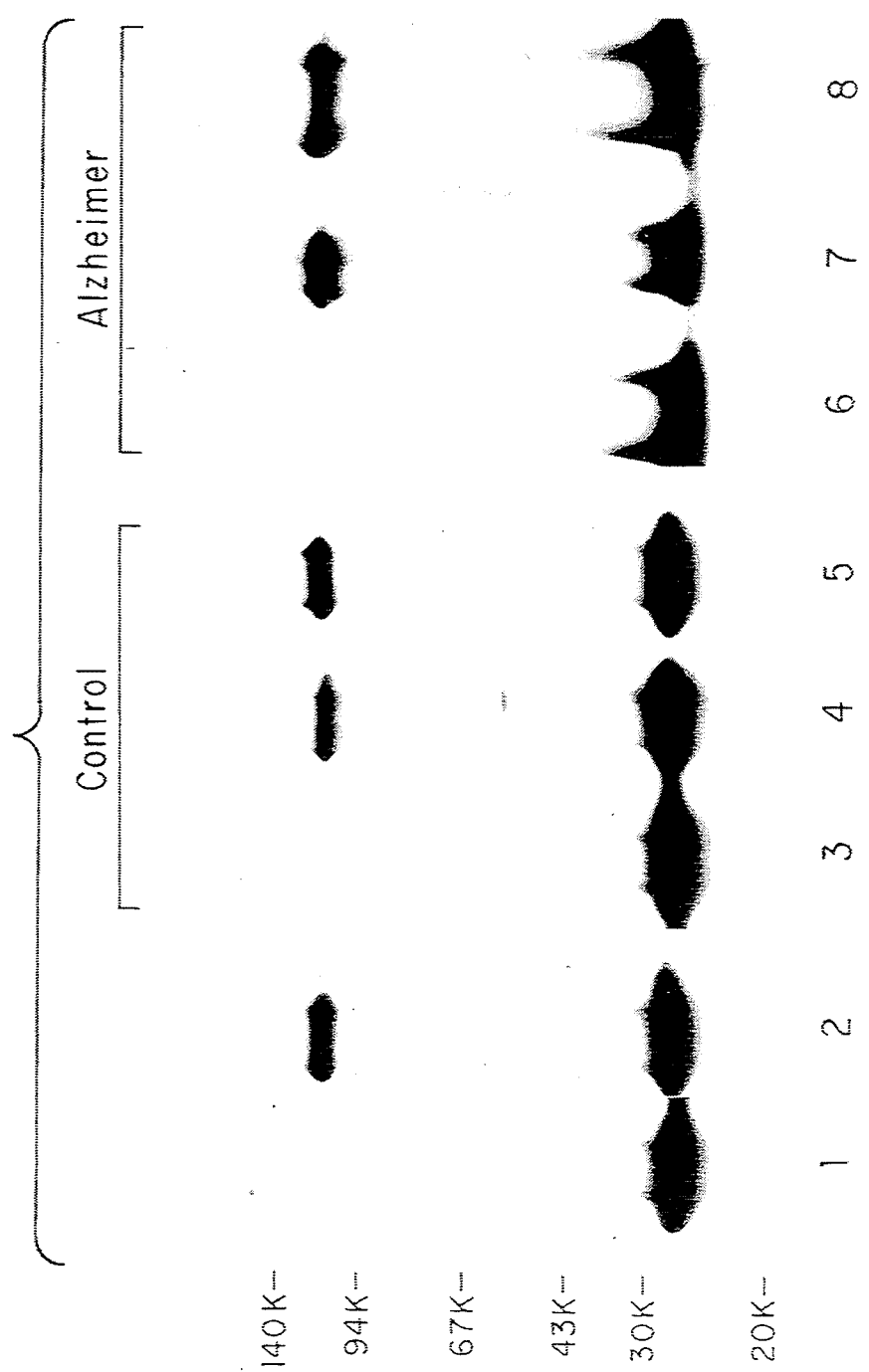
FIG. 6 is an autoradiogram showing $^{125}$I-EGF BP:PN-2/βAPP complex formation in platelet lysates.

The autoradiogram from Example 15 is shown in FIG. 6. Lane 1 was $^{125}I$-EGF BP alone; lane 2 was $^{125}I$-EGF BP+purified PN-2/βAPP; lanes 3 and 6 were $^{125}I$-EGF BP+plasma; lanes 4 and 7 were $^{125}I$-EGF BP+platelet lysates; and lanes 5 and 8 were $^{125}I$-EGF BP+Plasma+purified PN-2/βAPP (0.5 nM). Lanes 5 and 8 were run to clearly show that purified PN-2/βAPP in an equivalent amount of plasma and followed by the same fractionation procedure would be detected by this assay.

We also ran Western blots of gels of fractionated blood components. These assays showed the absence of PN-2/βAPP immunoreactivity in the fractionated plasma samples using the anti-PN-2/βAPP mouse monoclonal antibody mAbP2-1, described in Example 1, or affinity purified anti-PN-2/βAPP rabbit polyclonal IgG. In these experiments the plasma was fractionated as described above for the functional assays. Western blotting of unfractionated plasma samples also failed to reveal immunoreactivity for PN-2/βAPP or fragments of it (data not shown). In contrast, both anti-PN-2/βAPP antibodies clearly recognized PN-2/βAPP in the platelet lysates. The following are examples of these Western Blot assays we performed to further show that circulating PN-2/βAPP was localized to platelet fractions.

EXAMPLE 16—Western Blot for PN-2/βAPP using mAbP2-1

Samples of plasma and platelets from control and Alzheimer's disease patients were prepared as described in Example 15. Samples were subjected to 10% SDS-PAGE followed by electro-elution onto nitrocellulose membranes for 2.5 hours at 0.4 A in a Transblot unit (BioRad Laboratories). The membranes were gently agitated overnight at 25° C. in TBS (50 mM Tris-HCl, 150 mM NaCl, pH 7.5) containing 0.25% gelating to block unoccupied sites, and then incubated with mouse monoclonal mAbP2-1 hybridoma culture supernatant for 1 hour at 37° C. with gentle agitation. After several washes with TBS containing 0.05% Tween-20, bound mouse mAbP2-1 was detected with a biotinylated sheep anti-mouse IgG (Amersham) and a streptavidin-horseradish peroxidase complex. To develop the Western blots, 48 mg of 4 chloronapthol were dissolved in 16 ml of ice-cold methanol which was added to 80 ml of ice-cold TBS, followed by addition of 64 μl of $H_2O_2$. Results are shown in FIG. 7, panel A. Lane 1 was purified human fibroblast PN-2/βAPP; lane 2 was fractionated plasma from a healthy patient; lane 3 was platelet lysate from a healthy patient; lane 4 was fractionated plasma from an Alzheimer's patient; and lane 5 was platelet lysate from an Alzheimer's patient. These results clearly show that immunoreactivity in blood towards mAbP2-1 was found only in platelets of both healthy and Alzheimer's patients.

EXAMPLE 17—Western Blot for PN-2/βAPP using polyclonal IgG

Western blots were performed as described in Example 16 except that affinity purified rabbit polyclonal IgG was used as the primary antibody. Bound rabbit antibody was detected using a biotinylated donkey anti-rabbit IgG (Amersham) and a streptavidin-horseradish peroxidase complex. Results are shown in FIG. 7, Panel B, with lane designations as in Example 16. These results also show that PN-2/βAPP immunoreactivity in blood is found only in platelets of both healthy and Alzheimer's patients. To further show that platelets were a circulating source of PN-2/βAPP, monoclonal antibody mAbP2-1 was used to effectively immunopurify PN-2/βAPP from platelet lysates to apparent homogeneity using a method similar to that of Example 1. The following is an example of one such immunopurification procedure.

EXAMPLE 18—Immunopurification of PN-2/βAPP from Platelets

Approximately 10 units of outdated platelets were extensively washed and pelleted by centrifugation. They were then resuspended in 200 ml of 20 mM potassium phosphate, 0.15M NaCl, pH 7.4 containing 1% Triton X-100, 5 mM EDTA, 500 μM phenylmethane sulfonylfluoride, 10 μM chymostatin and 10 μM tosyl phenylchloromethyl ketone and solubilized with a Polytron. The homogenate was centrifuged at 10,000 x g for 30 minutes at 4° C.; the resulting supernatant was subjected to 40–80% ammonium sulfate precipitation. The 80% pellet was resuspended in 50 ml of 20 mM potassium phosphate, 0.2M NaCl pH7.4, dialyzed against the same buffer and chromatographed over a 10 ml DEAE-Sepharose column. The adsorbed protein was eluted with 20 mM potassium phosphate, 0.2M NaCl pH 7.4. The eluate was directly applied to a 3 ml immunoaffinity column of mAbP2-1-Sepharose, washed and eluted with 0.2M glycine-HCl, 0.15M NaCl, pH 2.7 followed by immediate neutralization with 2M Tris-HCl, pH 8.0. Five μg of the immunopurified PN-2/βAPP from platelets were subjected to 10% nonreducing SDS-PAGE followed by staining with Coomassie Brilliant Blue. This gel is shown in FIG. 7, Panel C. It can be seen that the purified PN-2/βAPP co-migrates with the PN-2/βAPP immunoreactive species from Examples 15 and 16, Panels A and B respectively.

EXAMPLE 19—Western Blot of Purified PN-2/βAPP

Two μg of purified PN-2/βAPP from Example 18 was subjected to Western Blot as in Example 16, except that rabbit polyclonal antiserum (1:200) was used as the primary antibody. Bound antibody was detected as in Example 17. Results are shown in FIG. 7, panel D. Lane 1 shows rabbit polyclonal antiserum to synthetic A4. Lane 2 was as in Lane 1, absorbed with synthetic A4.

It can be seen from FIG. 7, panel D that the immunopurified PN-2/βAPP from platelet lysates was recognized by rabbit polyclonal antiserum to synthetic A4, demonstrating that at least part of the A4 protein is present in PN-2/βAPP.

MECHANISM OF PN-2/βAPP RELEASE BY PLATELETS

In order to elucidate the mechanism by which platelets can make PN-2/βAPP available, freshly washed platelets were treated with collagen or thrombin, physiologic platelet agonists that trigger secretion of platelet granule constituents. We discovered that activation of platelets with either collagen or thrombin resulted in secretion of approximately one-half of total PN-2/βAPP present in the platelets. Similarly, low affinity platelet factor-4 ("LA-PF4"), an s-granule constituent, and adenine nucleotides which are dense granule constituents, were also secreted after treatment of platelets with either agonist. To determine the extent that the presence of PN-2/βAPP or the granule markers in the releasates was due to platelet lysis, we assayed for the cytosolic marker lactate dehydrogenase ("LDH") which would only be expected to be released upon lysis. No LDH was detected in the releasates, demonstrating that the release of PN-2/βAPP did not result from platelet lysis. Treatment of the platelets with metabolic inhibitors prior to activation by either agonist blocked the secretion of PN-2/βAPP and the granule markers, consistent with findings that platelet activation and granule secretion are active processes. The methods of the foregoing experiments are described in the following Example.

EXAMPLE 20—Secretion of PN-2/βAPP from platelets

Secretion of PN-2/βAPP from platelets after activation by the agonists collagen or thrombin was studied. Briefly, fresh platelets washed by albumin density gradient centrifugation and gel filtration were incubated for 30 minutes at 37° C. in the absence or presence of the combined metabolic inhibitors antimycin A (15 μg/ml), 2-deoxy-D-glucose (30 mM), and D-gluconic acid δ-lactone (10 mM). The platelets were then placed into a cuvette 37° C. water bath with stirring at 1,200 rpm, and collagen (20 μg/ml or α-thrombin (1 U/ml) was added. After 10 minutes, the samples were centrifuged at 12,000 x g for 4 minutes and supernatants were collected. Aliquots were removed and quantitated for PN-2/βAPP by incubation with $^{125}$I-EGF BP and analysis of complex formation by SDS-PAGE and autoradiography as in Example 15. Autoradiograms were aligned with dried gels; $^{125}$I-EGF BP:PN-2/βAPP complexes were located, excised and quantitated in a γ counter. Aliquots were also quantitated for platelet markers as follows: total adenine nucleotide (ADP/ATP) secretion was measured by the method of Homsen et al., *Anal. Biochem.*, 46:489 (1972); low affinity platelet factor 4

(LA-PF4) secretion was quantitated by the method of Rucinski et al., *Blood*, 53:47 (1979); and cytosolic lactate dehydrogenase (LDH) loss was assessed by the procedure of Wroblewski and Ladue, *Proc. Soc. Exper. Biol. Med.*, 90–210 (1955), the disclosures of which are hereby incorporated by reference. Results are summarized in Table III. Values represent the percent secreted. Percent secreted was determined from the ratio of releasate in agonist treated sample to the total amount present in detergent lysate; nonstimulated platelet supernatants were subtracted from both. Values expressed are the mean ±SEM of three experiments, each consisting of combined platelets from two donors.

The results of Table III suggested that PN-2/βAPP was most likely a platelet granule protein. Therefore, we conducted further studies to ascertain the specific subcellular localization of PN-2/βAPP. One study we conducted was platelet subcellular fractionation in-order to ascertain in which fraction PN-2/βAPP was found. The following example shows one such study.

EXAMPLE 21—Platelet Subcellular Fractionation by Differential Ultracentrifugation A platelet pellet was prepared from 450 ml of blood, resuspended in 25 ml 10 mM HEPES, 1 mM EDTA, and 0.25M sucrose and homogenized twice in a French pressure cell. Differential centrifugation of the homogenate, as described in Schmaier, et al., *J. Clin. Invest.*, 75:242 (1985), the disclosure of which is hereby incorporated by reference, resulted in four fractions: $F_1$, a 1,000 x g pellet which contained whole platelets and large platelet fragments; $F_2$, a 12,000 x g pellet which contained mitochondria and granules; $F_3$, a 100,000 x g pellet containing membranes, and $F_4$, a 100,000 x g supernatant containing cytosolic material. Aliquots of each fraction were quantitated for PN-2/βAPP as described in Example 20; fibrinogen was quantitated by the method of Laurell, *Anal. Biochem.*, 15:45 (1966), the disclosure of which is hereby incorporated by reference; and LA-PF4 by the procedure of Rucinski et al., supra. Only preparations that had a recovery of at least 60% for total protein and each constituent were used in the analysis. The relative specific amounts of each marker in the preparation were calculated from the ratio of the specific amount of marker in the fraction (amount of antigen or activity per mg total protein) to the specific amount of the marker in the total platelet lysate according to the convention of de Duve et al, *Biochem J.*, 60:604 (1955), the disclosure of which is hereby incorporated by reference. The product of the relative specific amount of marker and percent total protein indicates the percent marker found within the fraction. FIG. 8A represents a bar graph of the percent of each marker ±SEM found within each fraction of the differential centrifugation.

FIG. 8A shows that approximately 53% of the total PN-2/βAPP was recovered in the granule fraction $F_2$. Similar results were obtained for platelet fibrinogen and low affinity platelet factor-4, known α-granule proteins. Thus, this granule preparation was further fractionated by sucrose density ultracentrifugation, as shown in the following example.

EXAMPLE 22—Platelet Subcellular Fractionation by Sucrose Density Ultracentrifugation The granule fraction, $F_2$, from Example 21, was further fractionated on a sucrose step gradient that increased from 0.8 to 2.0M in 0.2M increments. Centrifugation resulted in four major fractions: A, material which did not enter the gradient; B, lysosomal granule constituents; C, α-granule constituents; and D, a pellet which consists of dense granules. PN-2/βAPP and fibrinogen were quantitated as in Example 20. Serotonin was assayed by the procedure of Weissbach et al., *J. Biol. Chem.*, 230: 865 (1955), the disclosure of which is hereby incorporated by reference. The data were calculated as in Example 21 and the results, shown in FIG. 8B, were plotted as in Example 21. Each bar graph, except for the serotonin, is the mean ±SEM of three experiments. The serotonin experiments are the mean of two identical experiments.

Figures 1, 8B:
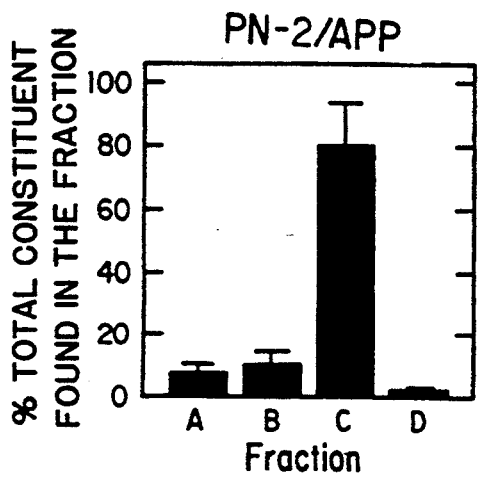
Figures 2, 8B:
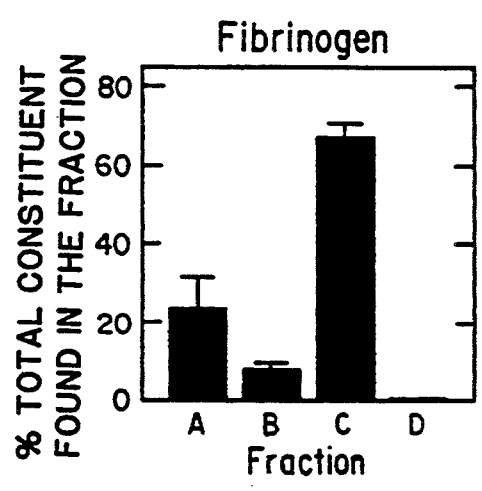
Figures 3, 8B:
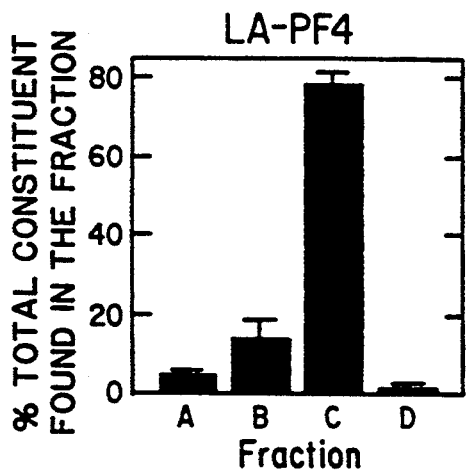
Figures 4, 8B:
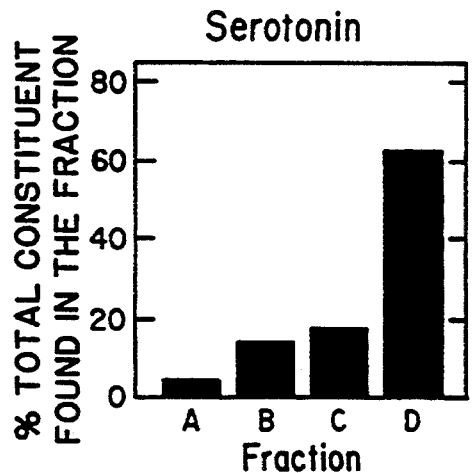

FIG. 8B shows that approximately 80% of the PN-2/βAPP activity in the granule fraction $F_2$ was recovered in fraction C which is enriched for platelet α-granules. Similar results were obtained for fibrinogen and low affinity platelet factor-4. In contrast, serotonin, a known dense granule constituent, was recovered almost exclusively in fraction D, a pellet of the sucrose gradient.

Thus, as the foregoing examples show, we have discovered that PN-2/βAPP does not circulate freely in plasma, but is contained in the α-granules of platelets. Moreover, the foregoing examples also show that we have further discovered that upon platelet activation, PN-2/βAPP is secreted along with other platelet α-granule constituents.

DIAGNOSIS OF ALZHEIMER'S

The results of the foregoing studies on the circulating source of PN-2/βAPP indicate a pathophysiologic mechanism for the deposition of cerebrovascular and peripheral perivascular PN-2/βAPP and A4. In these situations, subtle changes in the vessel walls of the vasculature, as may occur in certain malformations, may expose sites that could activate platelets and cause them to secrete their granule contents, including PN-2/βAPP and derived fragments, such as A4.

Platelets from individuals with Alzheimer's disease have alterations in their plasma membranes. We believe that this may contribute to increased platelet adherence to the vasculature and/or increased secretion of PN-2/βAPP or related fragments. Therefore, we believe that platelets of Alzheimer's patients have altered levels of PN-2/βAPP and related fragments. Due to the long lag time during which neuritic plaques are forming without causing symptoms, we believe that these altered levels of PN-2/βAPP may be detectable years before clinical symptoms appear.

Normal PN-2/βAPP is believed to contain at least a portion of A4. It is believed that proteolytic cleavage of this portion of A4 occurs. Thus, fragments of PN-2/βAPP slightly smaller than native PN-2/βAPP lacking the portion of A4 can be detected in normal subjects by Western assay using mAbP2-1 as a probe. It is possible that there is an increase in this proteolytic cleavage in Alzheimer's disease. Thus, increased amounts of this smaller fragment may be present in Alzheimer's disease patients.

As stated above, one theory is that PN-2/βAPP from Alzheimer's patients contains all of A4 while PN-2/βAPP from normal subjects lacks at least a portion of A4. Thus, if this theory is correct, the detection of fragments of PN-2/βAPP slightly larger than native PN-2/βAPP by mAbP2-1 in Western assays would be indicative of Alzheimer's disease.

Accordingly, we have discovered methods for diagnosing Alzheimer's disease, which are effective not only prior to autopsy, but which are advantageously effective even prior to any clinical manifestations of the disease. One such method comprises obtaining platelets from a subject and determining the level of PN-2/βAPP or any fragment thereof in those platelets. An Alzheimer's patient will have significantly altered levels of PN-2/βAPP or a fragment thereof than normal subjects, even if the test is performed long before clinical manifestations appear.

Examples 23–27 are intended to illustrate typical methods of practicing this aspect of the present invention. In these examples, PN-2/βAPP is used to refer to PN-2, βAPP, or any fragment thereof.

EXAMPLE 23—Determination of Normal Levels of PN-2/βAPP in Platelets

Ten healthy 20 year old female patients are tested for platelet levels of PN-2/βAPP by drawing 25 cc of blood from each. Platelets are isolated and lysed, and the level of PN-2/βAPP determined by the method of Example 10. The levels of the native fragment of PN-2/βAPP are found to be in the range of 150 ng/$10^8$ platelets to 2 μg/$10^8$ platelets, with an average of 1 μg/$10^8$ platelets. A much smaller amount of the smaller fragment of PN-2/βAPP lacking all of the A4 region is detected.

EXAMPLE 24—Detection of Alzheimer's Disease through Platelet Levels of PN-2/βAPP A 60 year old female patient with no clinical symptoms of Alzheimer's disease is tested for Alzheimer's by drawing 25 cc of blood. Platelets are isolated and lysed, and the level of PN-2/βAPP determined by the method of Example 10. The level of the native fragment of PN-2/βAPP is found to be 100 ng/$10^8$ platelets, lower than the normal levels of determined in Example 23. The patient shows a higher level of the smaller fragment of PN-2/βAPP lacking the A4 region. The patient may also show detectable levels of the larger fragment of PN-2/βAPP having all of the A4 region. Thus, it is concluded that the patient has a high potential for developing Alzheimer's symptoms within the next few years. Appropriate treatment may then be provided.

Thus, the foregoing examples show quantitative and qualitative methods of the present invention in which platelet levels of the various fragments of PN-2/βAPP are indicative of Alzheimer's disease. These examples show that quantitative changes in the level of the native PN-2/βAPP may be used to diagnose Alzheimer's disease. Additionally, the qualitative findings of either the larger fragment of PN-2/βAPP containing most or all of the A4 region or the smaller fragment lacking the A4 region may also be indicative of Alzheimer's disease.

An additional method of the present invention is to detect Alzheimer's disease by altered levels of PN-2/βAPP in the CSF. An example of this method is shown in Example 25.

EXAMPLE 25—Determination of Normal Levels of PN-2/βAPP in CSF

Four healthy patients were tested for levels of PN-2/βAPP by drawing 3 cc of CSF from each. The level of PN-2/βAPP in each sample was determined by the method of Example 10 and by the method of Example 20. The levels of PN-2/βAPP were found to be in the range of 5 to 10 μg/ml, with an average of 7.5 μg/ml.

EXAMPLE 26—Detection of Alzheimer's Disease through CSF Levels of PN-2/βAPP

Four patients with varying clinical symptoms of Alzheimer's disease were tested for Alzheimer's by drawing 3 cc of CSF. The level of PN-2/βAPP in the CSF was determined by the method of Example 10. The level of PN-2/βAPP was found to be at least 50% lower than the normal levels determined in Example 25. Thus, the decreases in PN-2/βAPP in CSF correlated with neurodegeneration.

Thus, the Example 26 shows a method of the present invention in which CSF levels of PN-2/βAPP are indicative of Alzheimer's disease. We also believe that the increased secretion of PN-2/βAPP in Alzheimer's patients results in PN-2/βAPP being detectable in a wide variety of tissues in these patients. Thus, additional methods of the present invention may detect Alzheimer's disease by detecting altered levels of PN-2/βAPP in the any of a wide variety of tissues. Some particular tissues are believed to have normal levels of PN-2/βAPP that are substantially undetectable by the methods of the present invention in healthy patients, yet have elevated levels in Alzheimer's. Thus, for these tissues, the detection of any PN-2/βAPP is indicative of a disease state. These tissues include skin, subcutaneous tissue and intestine. It has been found that these tissues have normal levels of PN-2/βAPP in the range of 1 pg/mg tissue to 5 pg/mg tissue. The following example illustrates a method embodying this aspect of the present invention.

EXAMPLE 27—Detection of Alzheimer's Disease through Presence of PN-2/βAPP

A 62 year old male patient with no clinical symptoms of Alzheimer's disease is tested for Alzheimer's by first obtaining a small sample of skin from the top of the hand. The skin is homogenized and the level of PN-2/βAPP in the homogenate is determined by the method of Example 10. The level of PN-2/βAPP is found to be 0.5 pg/mg tissue. Thus, it is concluded that the patient has a high potential for developing Alzheimer's symptoms within the next few years. Appropriate treatment may then be provided.

COAGULATION INHIBITION

Our discoveries that PN-2/βAPP is an α-granule constituent of platelets and that it may be secreted upon platelet activation are particularly significant when combined with recent reports that PN-2/βAPP possesses growth factor activity. It is known that platelets aggregate at wound sites and secrete the contents of their storage granules which include growth factors. Moreover, wound sites also contain elevated levels of proteases which: (a) mediate formation of the fibrin clot, (b) participate in tissue repair by stimulating cell division and cell migration, and (c) influence inflammatory response. Thus, we believe that PN-2/βAPP, which has both protease inhibitory activity and growth factor activity is involved in the complex events that lead to tissue repair.

In particular, PN-2/βAPP has Factor XIa inhibitory activity. The kinetic studies of Example 8, reported in Table II, show that PN-2/βAPP is a potent inhibitor of coagulation factor XIa, suggesting that PN-2/βAPP may be a modulator of the blood clotting cascade. Factor XIa is critical in the events leading to blood coagulation. The inhibition of Factor XIa blocks nearly the entire cascade. Thus, we have discovered that PN-2/βAPP can be successfully used as an anti-coagulation agent in mammals. Anti-coagulation treatment is useful in treating a variety of diseases in which blood clots may cause severe disabilities, such as myocardial infarction, phlebitis, stroke and other diseases.

Accordingly, in certain preferred embodiments of the present invention, PN-2/βAPP or an analog thereof is formulated into pharmaceutical preparations having anti-coagulation activity. These pharmaceutical preparations may further include other pharmaceutically active ingredients. In addition, any of the well-known pharmaceutically acceptable carriers or excipients may be combined with PN-2/βAPP in well-known manner. Administration may be intramuscular, intravenous, intraperitoneal or by any other known method of delivering a pharmaceutical.

Therapeutic dosage of PN-2/βAPP or an analog thereof when used intravenously in accordance with a method of the preferred embodiment for anti-coagulation is preferably in the range of 600 μg to 60 mg for a 70 kilogram adult per day, more preferably in the range of 3 mg to 12 mg active ingredient for a 70 kilogram adult per day. The total amount of active ingredient administered per day is preferably divided into two to four equal dosages per day.

EXAMPLE 28—An Anti-Coagulant Composition for Intravenous Injection 1 mg/ml PN-2/βAPP balance sterile $H_2O$ EXAMPLE 29—Anti-Coagulant Treatment of Phlebitis with PN-2/βAPP The composition of Example 28 is injected intravenously by five patients suffering from phlebitis of the leg. Five matched control patients receive the composition of Example 28 lacking active ingredient. The composition is taken two times per day for a period of three months. At the end of the three month period, the five patients receiving the control composition have unchanged symptoms. In contrast, the five patients receiving PN-2/βAPP show increased blood flow through the leg relative to the start of this study.

EXAMPLE 30—Anti-Coagulant Treatment of Stroke with PN-2/βAPP

The composition of Example 28 is taken intravenously by five patients who are recent victims of stroke. Five matched control patients receive the composition of Example 28 lacking active ingredient. The composition is taken two times daily for a two year period. By the end of the two year period, four out of five of the control group suffer repeat strokes, with two patients dying. In the same period none of the PN-2/βAPP-treated group has suffered a repeat stroke, and all are living.

It will be appreciated that certain variations may suggest themselves to those skilled in the art. The foregoing detailed description is to be clearly understood as given by way of illustration, the spirit and scope of this invention being limited solely by the appended claims.

What is claimed is:
1. The monoclonal antibody producing strain ATCC No. HB 10424.
2. Monoclonal antibody produced by hybridoma strain ATCC No. HB 10424.

* * * * *